US00PP20100P2

(12) United States Plant Patent
Lemon

(10) Patent No.: US PP20,100 P2
(45) Date of Patent: Jun. 16, 2009

(54) ***GERANIUM* PLANT NAMED 'OGLGER12055'**

(50) Latin Name: *Pelargonium×hortorum*
Varietal Denomination: Oglger12055

(75) Inventor: David Lemon, Lompoc, CA (US)

(73) Assignee: Ecke Geraniums, LLC, Encinitas, CA (US)

( * ) Notice: Subject to any disclaimer, the term of this patent is extended or adjusted under 35 U.S.C. 154(b) by 0 days.

(21) Appl. No.: 12/156,718

(22) Filed: Jun. 3, 2008

(51) Int. Cl.
*A01H 5/00* (2006.01)

(52) U.S. Cl. ..... Plt./325
(58) Field of Classification Search ..... Plt./325
See application file for complete search history.

*Primary Examiner*—Kent L Bell
(74) *Attorney, Agent, or Firm*—C. A. Whealy

(57) ABSTRACT

A new and distinct cultivar of Zonal *Geranium* plant named 'Oglger12055', characterized by its upright, outwardly spreading and mounded plant habit; freely branching habit; freely and early flowering habit; pink and red bi-colored flowers; and good garden performance.

1 Drawing Sheet

Botanical designation: *Pelargonium×hortorum*.
Cultivar denomination: 'Oglger12055'.

BACKGROUND OF THE INVENTION

The present invention relates to a new and distinct cultivar of Zonal *Geranium*, botanically known as *Pelargonium×hortorum*, and hereinafter referred to by the name 'Oglger12055'.

The new Zonal *Geranium* is a product of a planned breeding program conducted by the Inventor in Lompoc, Calif. The objective of the breeding program is to create new vigorous Zonal *Geranium* cultivars with dark green-colored foliage and attractive and unique flower coloration.

The new Zonal *Geranium* originated from a cross-pollination made by the Inventor in June, 2001 in Lompoc, Calif. of a proprietary selection of *Pelargonium×hortorum* identified as code number 7338, not patented, as the female, or seed, parent with a proprietary selection of *Pelargonium×hortorum* identified as code number 8133, not patented, as the male, or pollen, parent. The cultivar Oglger12055 was discovered and selected by the Inventor as a flowering plant from within the progeny of the stated cross-pollination in a controlled environment in Lompoc, Calif. in March, 2002.

Asexual reproduction of the new Zonal *Geranium* by vegetative terminal cuttings in a controlled environment in Connellsville, Pa. since January, 2003, has shown that the unique features of this new Zonal *Geranium* are stable and reproduced true to type in successive generations.

SUMMARY OF THE INVENTION

The cultivar Oglger12055 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Oglger12055'. These characteristics in combination distinguish 'Oglger12055' as a new and distinct cultivar of Zonal *Geranium*:

1. Upright, outwardly spreading and mounded plant habit.
2. Freely branching habit.
3. Freely and early flowering habit.
4. Pink and red bi-colored flowers.
5. Good garden performance.

Plants of the new Zonal *Geranium* differ from plants of the female parent selection in the following characteristics:

1. Plants of the new Zonal *Geranium* are more compact than plants of the female parent selection.
2. Plants of the new Zonal *Geranium* flower earlier than plants of the female parent selection.

Plants of the new Zonal *Geranium* differ from plants of the male parent selection in the following characteristics:

1. Plants of the new Zonal *Geranium* have darker green-colored leaves than plants of the male parent selection.
2. Plants of the new Zonal *Geranium* and the male parent selection differ in flower color as plants of the male parent selection have white-colored flowers.

Plants of the new Zonal *Geranium* can be compared to plants of the *Pelargonium×hortorum* cultivar Balshorozle, disclosed in U.S. Plant Pat. No. 7,835. In side-by-side comparisons conducted in Connellsville, Pa. plants of the new Zonal *Geranium* differed from plants of the cultivar Balshorozle in the following characteristics:

1. Flower color pattern of plants of the new Zonal *Geranium* was more distinct than flower color pattern of plants of the cultivar Balshorozle.
2. Plants of the new Zonal *Geranium* and the cultivar Balshorozle differed in flower color as plants of the cultivar Balshorozle had pink and dark pink bi-colored flowers.

BRIEF DESCRIPTION OF THE PHOTOGRAPH

The accompanying colored photograph illustrates the overall appearance of the new Zonal *Geranium*, showing the colors as true as it is reasonably possible to obtain in colored reproductions of this type. Colors in the photograph may differ slightly from the color values cited in the detailed botanical description which accurately describe the colors of the new Zonal *Geranium*. The photograph comprises a side perspective view of a typical flowering plant of 'Oglger12055' grown in a container.

DETAILED BOTANICAL DESCRIPTION

The aforementioned photograph and following observations, measurements and values describe plants grown in Connellsville, Pa. in a glass-covered greenhouse during the summer and under conditions which closely approximate Zonal *Geranium* commercial production. During the production of the plants, day temperatures ranged from 21° C. to 32° C., night temperatures ranged from 17° C. to 21° C. and light levels ranged from 2,500 lux to 3,000 foot-candles. candles. Plants were about nine weeks from planting when the photographs and the description were taken. In the detailed description, color references are made to The Royal Horticultural Society Colour Chart, 2001 Edition, except where general terms of ordinary dictionary significance are used.

Botanical classification: *Pelargonium×hortorum* cultivar Oglger12055.

Parentage:

*Female, or seed, parent.*—Proprietary selection of *Pelargonium×hortorum* identified as code number 7338, not patented.

*Male or pollen parent.*—Proprietary selection of *Pelargonium×hortorum* identified as code number 8133, not patented.

Propagation:

*Type.*—By vegetative terminal cuttings.

*Time to initiate roots, summer.*—About ten days at temperatures of 20° C.

*Time to initiate roots, winter.*—About two weeks at temperatures of 16° C.

*Time to produce a rooted young plant, summer.*—About four weeks at temperatures of 20° C.

*Time to produce a rooted young plant, winter.*—About four weeks at temperatures of 16° C.

*Root description.*—Fine, fibrous; white in color.

*Rooting habit.*—Freely branching.

Plant description:

*General appearance.*—Upright and outwardly spreading plant habit; uniformly mounded; densely foliated.

*Growth and branching habit.*—Low vigor; freely branching habit.

*Plant height, to top of foliar plane.*—About 11.4 cm to 14.4 cm.

*Plant height, to top of umbels.*—About 22.3 cm to 30.2 cm.

*Plant width.*—About 26.6 cm to 29.1 cm.

*Main stems.*—Length: About 9.2 cm to 10.5 cm. Diameter: About 7 mm to 9 mm. Internode length: About 7 mm to 11 mm. Texture: Pubescent. Strength: Strong. Color: 143C.

*Primary lateral branches.*—Length: About 1.8 cm to 2.7 cm. Diameter: About 5 mm to 8 mm. Internode length: About 1.5 cm to 2.4 cm. Texture: Pubescent. Strength: Strong. Color: 143B.

Foliage description:

*Arrangement.*—Alternate, simple.

*Length.*—About 4.3 cm to 7.1 cm.

*Width.*—About 5.8 cm to 8.2 cm.

*Shape.*—Reniform.

*Apex.*—Rounded.

*Base.*—Cordate.

*Margin.*—Crenate.

*Venation pattern.*—Palmate.

*Texture, upper and lower surfaces.*—Pubescent; velvety.

*Color.*—Developing and fully expanded foliage, upper surface: 141A; venation, 141A. Developing and fully expanded foliage, lower surface: 141B; venation, 144A. Zonation pattern: Not observed.

*Petiole.*—Length: About 5.6 cm to 6.9 cm. Diameter: About 3 mm to 6 mm. Texture, upper and lower surfaces: Smooth, glabrous. Color, upper and lower surfaces: 141B.

Flower description:

*Flower arrangement.*—Rotate flowers arranged in rounded hemispherical umbels arising from apical leaf axils. Umbels displayed above the foliage on strong peduncles. Flowers face upright to outward; flowers slightly cupped becoming flatter with development. Flowers not persistent. Flowers not fragrant.

*Quantity of flowers.*—Freely flowering habit; about 14 to 19 flowers per umbel and about one to two umbels per lateral branch.

*Flowering season.*—In Connellsville, Pa., flowering is continuous during the spring and summer.

*Flower longevity.*—Individual flowers last about 10 to 14 days on the plant.

*Umbel height.*—About 4.5 cm to 5.2 cm.

*Umbel diameter.*—About 9.5 cm to 10.2 cm.

*Flower diameter.*—About 3.5 cm to 3.7 cm.

*Flower depth (height).*—About 1.5 cm to 1.7 cm.

*Flower buds.*—Length: About 9 mm to 13 mm. Diameter: About 3 mm to 5 mm. Shape: Elliptical.

*Petals.*—Quantity per flower: About five in a single whorl. Length: About 1.9 cm to 2.5 cm. Width: About 1.4 cm to 1.7 cm. Shape: Roughly spatulate. Apex: Rounded. Base: Attenuate. Margin: Entire. Texture, upper and lower surfaces: Smooth, glabrous. Color: When opening and fully opened, upper surface: Towards the margins, 65C, with random speckling, N57B; center, 46C; towards the base, close to N155C; upper two petals with venation, N57A. When opening and fully opened, upper two petals, lower surface: 65C; towards the base, 63D; venation, N57A. When opening and fully opened, lower three petals, lower surface: 65D.

*Petaloids.*—None observed.

*Sepals.*—Quantity per flower: Five, arranged in a single whorl. Length: About 2 cm. Width: About 5 mm. Shape: Lanceolate. Apex: Acute. Base: Attenuate. Margin: Entire. Color, upper and lower surfaces: Close to 144A.

*Peduncle (umbel stem).*—Length: About 14.7 cm to 15.7 cm. Diameter: About 3 mm to 4 mm. Strength: Strong. Texture: Pubescent. Color: Darker than 144A.

*Pedicel (individual flower stem).*—Length: About 3.6 cm to 4.3 cm. Diameter: About 1.5 mm to 2 mm. Strength: Strong. Texture: Pubescent. Color: Towards the peduncle, 152B to 152C; towards the sepals, 172A.

*Reproductive organs.*—Androecium: Stamen quantity per flower: About seven to eight. Filament length: About 3 mm to 7 mm. Filament color: Close to N155B. Anther length: About 1 mm to 1.5 mm. Anther shape: Oval; slightly curved. Anther color:

N57C. Pollen amount: Abundant. Pollen color: 28B. Gynoecium: Pistil quantity per flower: One. Pistil length: About 8 mm. Stigma shape: Split into five parts. Stigma size: About 2 mm. Stigma color: 53D. Style length: About 2 mm. Style color: 53D. Ovary color: 144B.

*Seed.*—Seed development has not been observed.

Disease/pest resistance:

Plants of the new Zonal *Geranium* have not been observed to be resistant to pathogens and pests, common to Zonal Geraniums.

Garden performance: Plants of the new Zonal *Geranium* have been observed to tolerate rain, wind, and temperatures ranging from about 1° C. to about 35° C. and have demonstrated good garden performance.

It is claimed:

1. A new and distinct Zonal *Geranium* plant named 'Oglger12055' as illustrated and described.

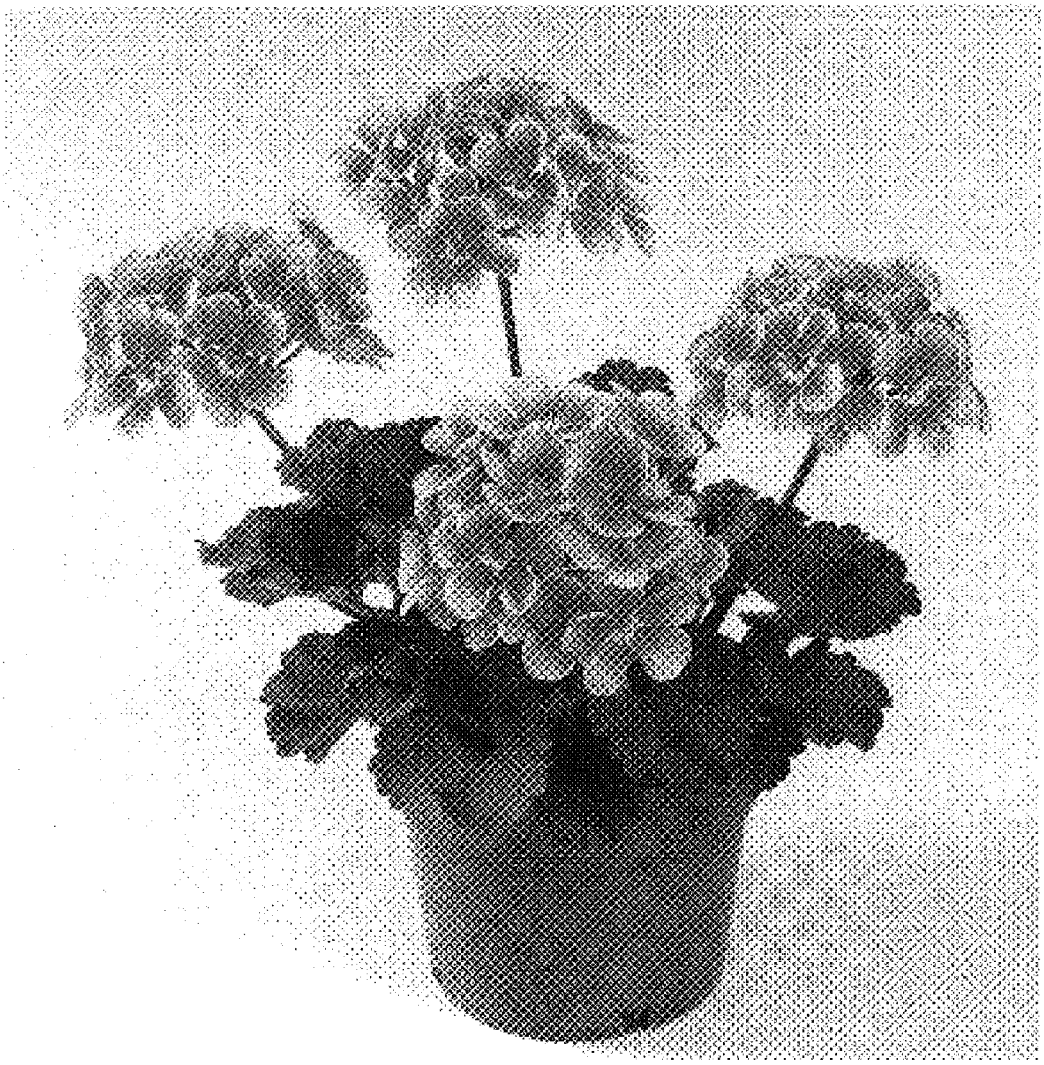

* * * * *